United States Patent
Weiss (10) Patent No.: US 10,035,002 B2
(45) Date of Patent: Jul. 31, 2018

(54) COMPOSITE FIBER GUIDEWIRES (75) Inventor: Steffen Weiss, Hamburg (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 453 days.

(21) Appl. No.: 14/125,737

(22) PCT Filed: Jun. 11, 2012

(86) PCT No.: PCT/IB2012/052933
§ 371 (c)(1),
(2), (4) Date: Dec. 12, 2013

(87) PCT Pub. No.: WO2012/176091
PCT Pub. Date: Dec. 27, 2012

(65) Prior Publication Data
US 2014/0121648 A1    May 1, 2014

(30) Foreign Application Priority Data
Jun. 23, 2011  (EP) .................... 11171149

(51) Int. Cl.
*A61B 5/00* (2006.01)
*A61M 25/09* (2006.01)
(Continued)

(52) U.S. Cl.
CPC .......... *A61M 25/09* (2013.01); *B29C 70/52* (2013.01); *A61B 5/01* (2013.01); *A61B 5/02154* (2013.01);
(Continued)

(58) Field of Classification Search
CPC ........ A61M 25/09; A61M 2025/09083; A61M 2025/09108; A61M 2025/09133
(Continued)

(56) References Cited

U.S. PATENT DOCUMENTS

| | | | |
|---|---|---|---|
| 4,563,181 A | | 1/1986 | Wijayarathna |
| 4,928,693 A | * | 5/1990 | Goodin et al. ............... 600/434 |

(Continued)

FOREIGN PATENT DOCUMENTS

| | | |
|---|---|---|
| CN | 101618249 A | 1/2010 |
| WO | 2006050385 A2 | 5/2006 |
| WO | 2007000148 A2 | 1/2007 |

OTHER PUBLICATIONS

Krueger, Sascha et al "An MR Guidewire Based on Micropultruded Fiber-Reinforced Material", Magnetic Resonance in Medicine, vol. 60, 2008, pp. 1190-1196.
(Continued)

*Primary Examiner* — Max Hindenburg (57) ABSTRACT

A guide wire (400, 500, 600, 700, 800, 900, 1000, 1200, 1300) is adapted for use in magnetic resonance imaging systems. The guide wire has a shaft region (402) and a distal tip region (404). The shaft region comprises a composite shaft (406) comprising reinforcing fibers aligned with a length extension (403) of the shaft region. The fibers extend at least partially into the distal tip region. The fibers form a taper (410) within the distal tip region. The distal tip region comprises a sensor (504, 604, 702, 704, 804, 904, 1006, 1008). The shaft comprises a cable (502, 602, 702, 704, 802, 902, 1002, 1004). The cable is connected to the sensor.

20 Claims, 9 Drawing Sheets

(51) Int. Cl.
  *B29C 70/52* (2006.01)
  *A61B 5/01* (2006.01)
  *A61B 5/0215* (2006.01)
  *A61B 5/055* (2006.01)
  *A61B 5/11* (2006.01)

(52) U.S. Cl.
  CPC ............. *A61B 5/055* (2013.01); *A61B 5/11* (2013.01); *A61B 5/6851* (2013.01); *A61B 2562/12* (2013.01); *A61M 2025/09108* (2013.01); *A61M 2025/09133* (2013.01); *A61M 2025/09175* (2013.01)

(58) Field of Classification Search
  USPC ........................................................ 600/585
  See application file for complete search history.

(56) References Cited

U.S. PATENT DOCUMENTS

| | | | |
|---|---|---|---|
| 5,251,640 A | 10/1993 | Osborne | |
| 5,451,209 A * | 9/1995 | Ainsworth et al. | 604/103.09 |
| 5,507,729 A | 4/1996 | Lindenberg | |
| 5,596,996 A * | 1/1997 | Johanson et al. | 600/585 |
| 5,701,905 A * | 12/1997 | Esch | 600/486 |
| 5,989,376 A | 11/1999 | Kusy | |
| 6,336,906 B1 * | 1/2002 | Hammarstrom et al. | 600/585 |
| 6,458,088 B1 | 10/2002 | Hurtak | |
| 6,475,226 B1 * | 11/2002 | Belef et al. | 606/185 |
| 6,508,806 B1 * | 1/2003 | Hoste | 604/524 |
| 6,918,920 B1 | 7/2005 | Wang | |
| 7,507,211 B2 * | 3/2009 | Pacetti et al. | 600/585 |
| 7,532,920 B1 | 5/2009 | Ainsworth | |
| 7,632,237 B2 * | 12/2009 | Murayama et al. | 600/585 |
| 7,682,352 B2 * | 3/2010 | Rafiee et al. | 604/532 |
| 7,722,237 B2 * | 5/2010 | Watson et al. | 362/559 |
| 7,896,820 B2 * | 3/2011 | Satou et al. | 600/585 |
| 7,967,761 B2 * | 6/2011 | Smith | 600/585 |
| 8,197,424 B2 | 6/2012 | Nabeshima | |
| 8,206,837 B2 * | 6/2012 | Mishima | 428/615 |
| 8,277,386 B2 * | 10/2012 | Ahmed et al. | 600/488 |
| 2002/0058888 A1 | 5/2002 | Biagtan | |
| 2002/0062091 A1 | 5/2002 | Jacobsen | |
| 2008/0021208 A1 | 1/2008 | Gallop | |
| 2008/0212082 A1 | 9/2008 | Froggatt et al. | |
| 2008/0312597 A1 | 12/2008 | Uihlein | |
| 2010/0063379 A1 | 3/2010 | Pfeffer | |
| 2010/0228112 A1 | 9/2010 | Von Malmborg | |
| 2010/0280359 A1 | 11/2010 | Kocaturk | |

OTHER PUBLICATIONS

Mekle, Ralf et al "A Polymer-Based MR-Compatible Guidewire: A Study to Explore New Prospects for Interventional Peripheral Magnetic Resonance Angiograph (ipMRA)", Journal of Magnetic Resonance Imaging, vol. 23, 2006, pp. 145-155.

Miles, Robin "Articulating Catheter Tip for Catheter Guidance", 2009.

* cited by examiner

COMPOSITE FIBER GUIDEWIRES

CROSS-REFERENCE TO PRIOR APPLICATIONS

This application is the U.S. National Phase application under 35 U.S.C. § 371 of International Application No. PCT/IB2012/052933, filed on Jun. 11, 2012, which claims the benefit of European Patent Application No. 11171149.5, filed on Jun. 23, 2011. These applications are hereby incorporated by reference herein.

TECHNICAL FIELD

The invention relates to guidewires for guiding a catheter or used stand-alone for in-body sensing, in particular to guidewires that are suitable to be guided using magnetic resonance imaging.

BACKGROUND OF THE INVENTION

Guidewires are mostly used to guide catheters. Standard guidewires used in interventional X-ray are passive devices made from conductive materials, mostly metals. They are easily visualized in X-ray projections and CT by their radio-opacity due to metal contents. Active guidewires are important as well in clinical practice. The use of active guidewires for measurement of pressure, temperature, and flow is common in interventional X-ray.

In magnetic resonance imaging, a large magnetic field is used to align the nuclear spins of atoms as part of the procedure for producing images within the body of a subject. Magnetic resonance imaging is typically used to map the location of protons, such as those in a water molecule, within a subject. Magnetic resonance imaging is much better than X-ray techniques such as CT at imaging soft tissues and showing the detailed anatomical structures of soft tissues. However, the large magnetic field and radio-frequency signals used for magnetic resonance imaging prevents the use of some materials and electronics during a magnetic resonance imaging scan.

SUMMARY OF THE INVENTION

The invention provides for a guidewire, a catheter system, and a method of manufacturing a guidewire for a catheter in the independent claims. Embodiments are given in the dependent claims.

A difficulty with integrating a sensor into a guidewire is that active guidewires would contain long conductors for wiring which may cause RF-heating problems in the guide wire. Embodiments of the invention may address the problem and others with a guidewire constructed from a composite shaft with fibers aligned with the length of the shaft. The fibers have a low electrical conductivity and a low magnetic susceptibility. The fibers may for instance the fibers may be, but are not limited to: non-conductive and non-magnetic fibers, dielectric fibers, glass fibers, carbon fibers, and aramid fibers. The composite shaft is magnetic resonance imaging compatible. A cable may be integrated into the composite shaft or attached to an outer surface of the shaft. For example, the cable may be a fiber optic cable or a resistive wire cable. The composite shaft may for instance be a fiber-reinforced core that may be co-pultruded with such wires/signal fibers, their connection to active components/sensors in the tip. Both types may be compatible with magnetic resonance imaging. This enables a sensor to be incorporated into the tip of a magnetic resonance imaging compatible guidewire.

Pultrusion as used here encompasses a continuous process for manufacture of composite materials. The composite material may have a constant cross-section. A pultrusion process may function by embedding fibers in a resin which is then formed with the fibers. For example a resin such as a thermosetting polymer may be used in conjunction with a heated die to form the composite material.

In one aspect the invention provides for a guidewire. In some embodiments the guidewire is adapted for guiding a catheter. In other embodiments the guidewire is adapted for use independent of a catheter. The guidewire has a shaft region and a distal tip region. The shaft region comprises a composite shaft comprising fibers aligned with a length extension of the shaft region. In some embodiments the fibers may extend along the entire length of the composite shaft. The fibers of the composite shaft extend at least partially into the distal tip region. This allows a surgeon to better manipulate the guidewire and steer it and it prevents vessel injury. The distal tip region comprises a sensor. The shaft region comprises a cable. The cable for instance may be attached to an outer surface of the composite shaft or the cable may be embedded into the composite shaft. The cable is connected to the sensor. The cable enables the sensor to be used for performing a measurement with the sensor.

This embodiment may have several advantages. The construction of the guidewire using the composite shaft comprising low conductivity and low magnetic susceptibility fibers, such as dielectric fibers, enables the guidewire to be used in a magnetic resonance imaging system. For instance a physician may use the magnetic resonance imaging for guiding the use of the guidewire. This is advantageous because ionizing radiation is not needed to see the position of the guidewire. In addition use of magnetic resonance imaging enables soft tissues to be better imaged. The incorporation of the sensor into the distal tip region enables vital measurements to be made with the guidewire when it has been inserted or when the catheter is being used. A portion of the fibers is extending into the distal tip regions allows the flexibility of the distal tip region to be controlled or adjusted with respect to the flexibility of the shaft region. In this way guidewires which have the appropriate flexibility in the distal tip region may be designed.

In another embodiment the shaft region and the distal tip region are enclosed within a coating. The coating may for instance, but is not limited to, be a bio-compatible coating. The use of the coating is beneficial because it may be coated such that the surface of the guidewire is smooth which enables it to be inserted into a subject. The use of a bio-compatible coating is beneficial because it reduces the chance that the guidewire will cause irritation or a reaction by the subject, e.g. formation of blood clots at the surface of the guide wire.

In another embodiment the cable is within the composite shaft. For instance when the composite shaft is manufactured the cable may be built directly into the composite shaft. This may be advantageous because the composite shaft protects the cable.

In another embodiment the cable is a fiber optic cable. This may be beneficial because the fiber optic may be incorporated directly into the composite shaft. For instance if the composite shaft is manufactured using a pultrusion process the fiber optic can be incorporated directly into the composite shaft during manufacturing. The composite shaft will provide an excellent protection of the fiber optic cable with minimal weight and size.

In another embodiment the sensor is a thermometer. The thermometer is a sensor which is connected to the fiber optic cable or a resistive wire. The thermometer sensor may also be a part of the optical fiber. This enables the temperature at the distal tip region to be measured without the use of wires and is therefore more magnetic resonance imaging compatible.

In another embodiment the sensor is an accelerometer attached to the fiber optic cable. The use of a fiber optic accelerometer enables the measurements of acceleration in the distal tip region without the use of wires.

In another embodiment the sensor is a pressure sensor. The pressure sensor is attached and operated by the fiber optic cable. The use of a fiber optic cable with a pressure sensor is beneficial because the pressure may be measured in the distal tip region without use of wires.

In another embodiment the sensor is an optical reflection spectrum sensor. The fiber optic cable may have one or more than one fibers which make up the fiber optic cable. For a single fiber light may be shown into a region of the subject and reflected light may be measured. This may be beneficial because the optical reflection properties of a tissue region surrounding the distal tip region may be measured.

In another embodiment the sensor is an optical reflection spectrum sensor attached to a fiber optic cable. The optical reflection spectrum sensor may use for instance one or two fiber optics to determine the optical reflection properties of tissue in the subject surrounding the distal tip region.

In another embodiment the sensor is an optical transmission spectrum sensor. Again one, two or more fibers may be in the fiber optic cable and may be used for measuring the optical transmission spectrum. This is also beneficial because optical transmission properties of tissue surrounding the distal tip region can be measured.

In another embodiment the sensor is an optical fluorescence spectrum sensor. For instance a single fiber may be used to illuminate tissue surrounding the distal tip region. The same fiber optic or a different fiber optic or fibers may be used to then channel the fluorescing light back to a spectrometer to measure the fluorescence. This may be useful for detecting and determining tissue properties in a region surrounding the distal tip region.

In another embodiment the fiber optic cable comprises two or more single core optical fibers. The fiber optic cable is the sensor. The fiber optic cable is a fiber optic positioning and/or shape sensor. The fiber optic cable may for instance be used as a sensor for a position and/or shape sensing based on Rayleigh scattering. Such a fiber optic sensor is disclosed in United States Patent Application publication US 2008/0212082 A1.

In another embodiment the single core optical fibers are used as a sensor for Bragg scattering strain-sensors to detect a deflection or the shape of the composite shaft.

In another embodiment the cable is attached to the composite shaft. For instance the cable may be attached to an outer surface of the composite shaft.

In another embodiment the cable attached to the composite shaft is a fiber optic cable.

In another embodiment the cable attached to the composite shaft is a resistive wire. The resistive wire in another embodiment may also be incorporated into the composite shaft. For instance, during a pultrusion process the cable may be incorporated into the composite shaft. The use of a resistive wire is beneficial because it enables the use of sensors which need a wire but the use of a resistive wire enables the wire to be used in a high rf field such as generated by a magnetic resonance imaging system.

In another embodiment the sensor is a temperature sensor. For instance the temperature sensor may be a thermocouple connected to two resistive wires.

In another embodiment the sensor is pressure sensor.

In another embodiment the sensor may be an electrophysiological potential sensor such as is used for ECG or electrocardiogram. The use of an electrophysiological potential sensor may be beneficial because the guidewire can be inserted near the region of a heart and measurements can be taken directly using the guidewire.

In another embodiment the composite shaft further comprises a first matrix material for binding the fibers together. The fibers in the distal tip region are connected with a second matrix material for binding the fibers. The flexibility of the second matrix material is higher than the first matrix material. This may be beneficial because the use of a different matrix material within the tip region may make the distal tip region of the guidewire more flexible. For instance when the wire is manufactured the matrix material of the composite may be removed in the distal tip region. The distal tip region may then be shaped and then re-glued or re-bound together using the second matrix material. This method alone or a combination with tapering the tip of the distal tip region enables the design of more highly flexible distal tip regions.

In another embodiment the fibers form a taper within the distal tip region. The tapering of the fibers in the distal tip region may make the distal tip region more flexible In another aspect the invention provides for a catheter system comprising a guidewire according to an embodiment of the invention and a catheter. The guidewire is configured for guiding the catheter. Catheters such as those already known in the art may be used with an appropriate guidewire according to the embodiment of the invention. This enables the design of a catheter system which is magnetic resonance compatible. The catheter system may be a catheter kit comprising a guide wire according to an embodiment of the invention and a catheter.

In another aspect the invention provides for a guidewire system comprising a guidewire according to an embodiment of the invention and sensor electronics or sensor optics. The sensor electronics or sensor optics are adapted to be connected to a proximal end of the guidewire. When connected to the proximal end of the guidewire the sensor electronics or sensor optics are connected to the cable. This enables to drive and/or receive data from the sensor. For connection of the cable to the electronics or optics, the matrix material may be removed at the proximal end as described above for connection of the distal end of the cable to the sensor.

In another aspect the invention provides for a method of manufacturing a guidewire for a catheter. The method comprises the step of receiving a composite shaft comprising fibers aligned with the length extension of the composite shaft. The composite shaft comprises a cable. The method further comprises the step of shaping the distal tip region of the composite shaft into a taper. The distal tip region may be shaped into a taper in a variety of different ways. For instance the distal tip region may be ground and/or the distal tip region may be formed by cutting individual fibers which make up the composite shaft within the distal region.

In still yet other embodiments the matrix material is removed from the distal tip region of the composite shaft, the distal tip region is shaped and then the distal tip region is then bound together using an additional binding agent or glue. The method further comprises the step of connecting a sensor to the cable. The cable is connected to the sensor to allow a sensor measurement or reading to be performed at a proximal end of the guide wire. For instance the cable may be a fiber optic or it may be a resistive wire. An embodiment of this invention may be beneficial because a magnetic resonance compatible guidewire may be constructed. Another potential benefit is that the tapered distal tip region of the composite shaft allows the precise design of the desired flexibility for the distal tip region. The method further comprises the step of connecting a sensor to the cable.

In another embodiment the method further comprises the step of coating the shaft region and the distal tip region with a coating. The coating may in some embodiments be a bio-compatible coating.

In another embodiment the method further comprises forming the composite shaft with a pultrusion process. The shaft could then be cut to the required length. The distal tip region of the composite shaft may be is provided by cutting it to length. The tip may be then formed into a taper-shape.

In some embodiments, the cable is incorporated into the composite shaft during the pultrusion process. For instance a large spool of the composite shaft could be manufactured at one time. Incorporating the cable into the composite shaft may be beneficial because it may make the catheter more easy and cost effective to manufacture. Incorporating the cable into the composite shaft may also make the cable better protected.

In other embodiments the composite shaft is pultruded, but the cable is attached to an exterior surface of the composite shaft.

In another embodiment the method may comprise the step of coating the shaft region and the distal tip region with a coating. For instance the coating may be a bio-compatible coating.

In another embodiment the fiber optic cable comprises two or more single core optical fibers. The fiber optic cable is the sensor. The fiber optic cable is a fiber optic position and/or shape sensor.

In another embodiment the method further comprises attaching the cable to an exterior surface of the composite shaft. For instance the cable may be glued or otherwise attached to a surface of the composite shaft.

In another embodiment the cable is a fiber optic cable.

In another embodiment the cable is a resistive wire.

In another embodiment the distal tip region is at least partially shaped by grinding. The composite material which makes up the composite shaft may be ground into a taper-shape. This may be beneficial because it is an easy and cost effective way of shaping the distal tip region.

In another embodiment the composite shaft further comprises a first matrix material for binding the fibers together. The method further comprises the step of removing the first matrix material at the distal tip region. For instance the distal tip region may be dipped into a solvent or other material which dissolves or removes the first matrix material. This may be beneficial because it may provide better access to the cable which to attach to the sensor. It may also be beneficial because removing the first matrix material from the distal tip region may make the distal tip more flexible.

In another embodiment the distal tip region is at least partially shaped by cutting a portion of the fibers. For instance once the first matrix materials have been removed from the distal tip region the individual fibers which make up the distal tip region may be cut.

In another embodiment the method further comprises the step of binding the fibers in the distal tip with a second matrix material for binding the fibers. The flexibility of the second matrix material is higher than the first matrix material. This embodiment may be beneficial because it allows reconstruction of the composite material in the distal tip region with a more flexible matrix material. This may facilitate the manufacture of a guidewire which has a distal tip region which has a higher flexibility.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
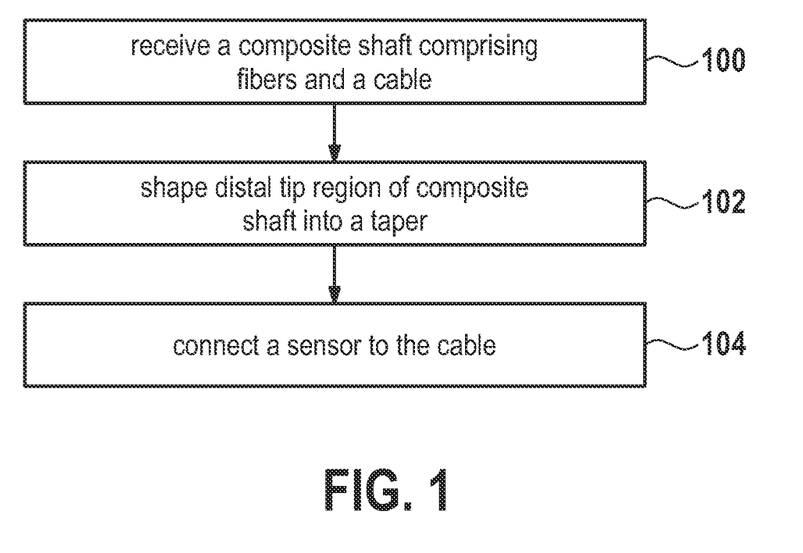
FIG. 1 shows a flowchart which illustrates a method according to an embodiment of the invention.

FIG. 1 shows a flowchart which illustrates a method according to an embodiment of the invention. In step 100 a composite shaft is received comprising fibers and a cable. For instance the cable may be formed into the fiber composite or it may be attached to an outside surface of the composite shaft. Next in step 102 a distal tip region of the composite shaft is shaped into a taper. Shaping the distal tip region into a taper allows the flexibility of the distal tip region to be increased. Finally in step 104 a sensor is connected to the cable.

Figure 2:
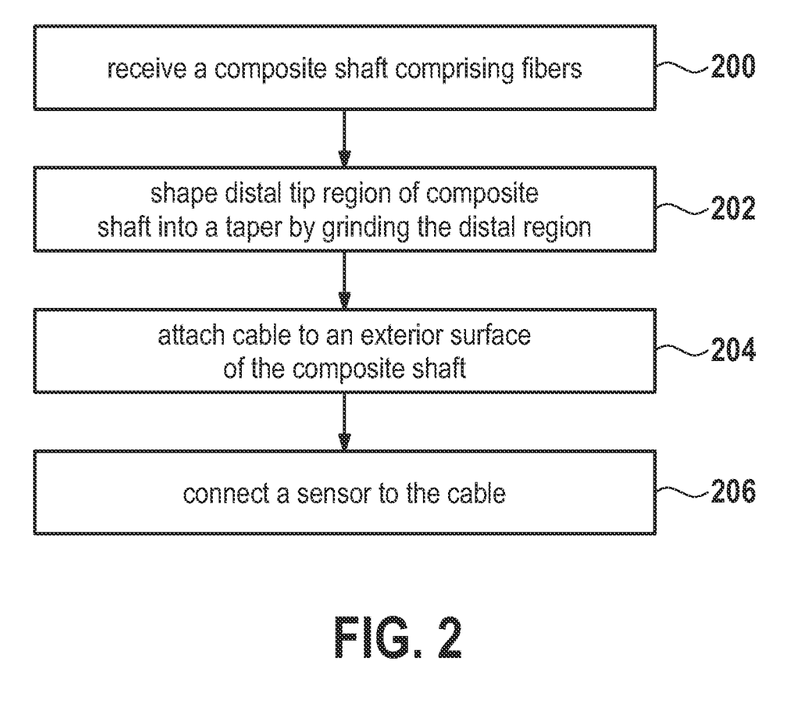
FIG. 2 shows a flowchart which illustrates a method according to a further embodiment of the invention.

FIG. 2 shows a flow diagram which illustrates a method according to a further embodiment of the invention. In step 200 a composite shaft is received comprising fibers. Next in step 202 the distal tip region of the composite shaft is shaped into a taper by grinding the distal tip region. Next in step 204 a cable is attached to an exterior surface of the cable. For instance the cable may be a resistive wire glued or otherwise attached to the exterior surface of the cable. Finally in step 206 a sensor is connected to the cable.

Figure 3:
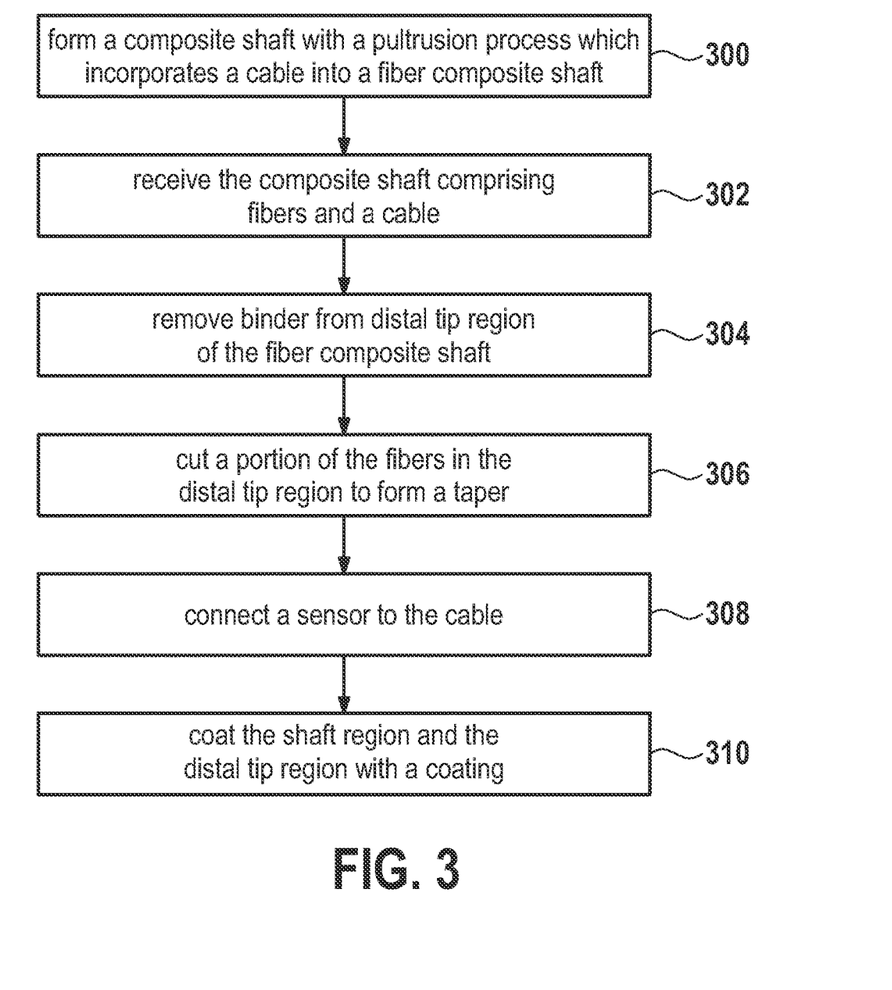
FIG. 3 shows a flowchart which illustrates a method according to a further embodiment of the invention.

FIG. 3 shows a flow diagram which illustrates the method according to a further embodiment of the invention. In step 300 a composite shaft is formed using a pultrusion process which incorporates a cable into a fiber composite shaft. Next in step 302 the composite shaft is received. For instance the composite shaft may be formed in a longer length and then cut to length. Next in step 304 the matrix material is removed from the distal tip region of the fiber composite shaft. The matrix material may for instance be the glue or other material which holds the fibers together. Next in step 306 a portion of the fibers in the distal tip region are cut to form a taper. In some embodiments the fibers may also be ground or ground prior to removing the matrix material. Next in step 308 a sensor is connected to the cable. Next in step 310 the shaft region and the distal tip region are coated with a coating. The coating for instance may be a bio-compatible coating.

Figure 4:
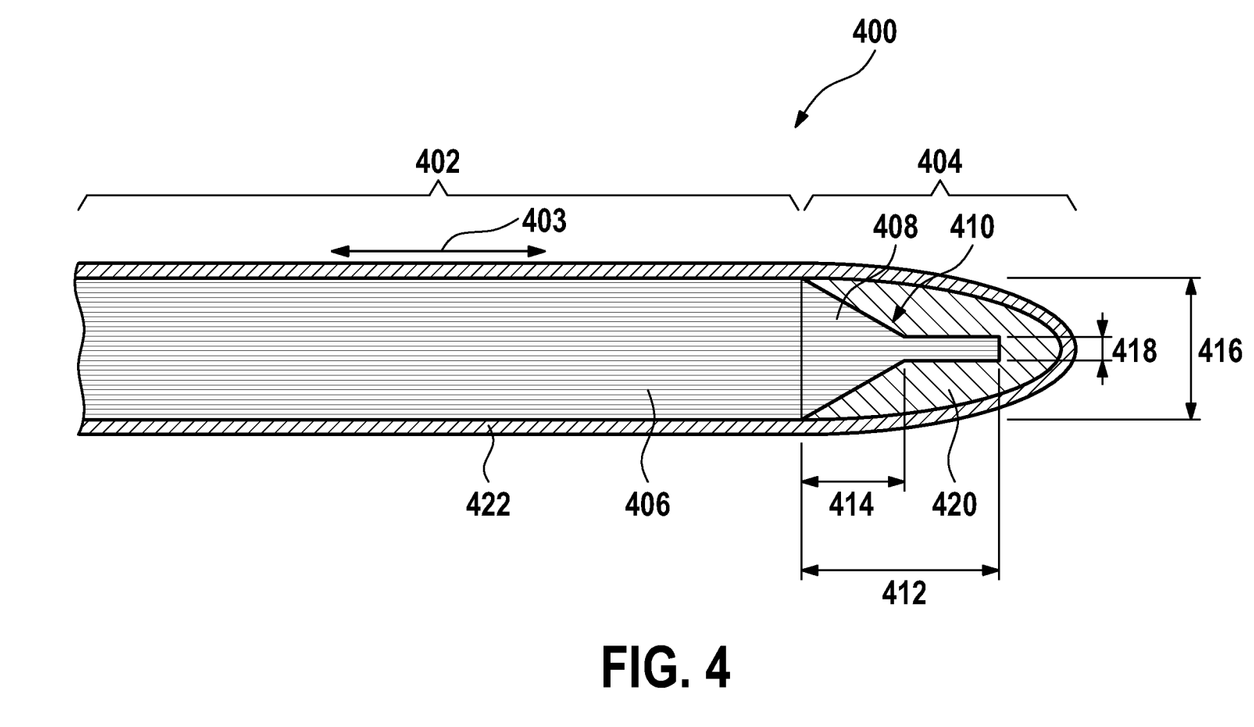
FIG. 4 illustrates a guidewire according to an embodiment of the invention.

FIG. 4 shows an example of a guidewire 400 according to an embodiment of the invention. In this particular embodiment the cable and the sensor are not shown. FIG. 4 illustrates the structure of a guidewire. Guidewire 400 comprises a shaft region 402 and a distal tip region 404. The arrow labeled 403 illustrates the length extension running along the length of the shaft region 402. Within the shaft region 402 the composite comprises fibers aligned with the length extension 403 and a region of a first matrix material 406. In the distal tip region 404 the fibers are again aligned with the length extension 403 but in this case may be formed with a second matrix material or glue 408. In some embodiments the second matrix material is equivalent or the same as the first matrix material. The composite material 408 has been ground down to a taper or shaped into a taper 410. The actual shape of the taper may be adjusted to adjust the floppiness or flexibility of the distal tip region 404. The overall length of the composite material 412 may be adjusted or changed in relation to the length of the taper 414. In many embodiments the length 414 of the taper 410 will be approximately 5 to 10 cm. In this case the guidewire is formed by a composite material of an outer diameter 416. The outer diameter will typically be 0.5 to 1 mm. The taper then narrows to a second diameter 418. In some embodiments the inner diameter 418 can be reduced to 0 and the taper 410 goes to a point. In other embodiments the length 412 and length 414 may be identical. In other embodiments the taper 410 may be a curved or other shaped surface. The taper 410 does not need to be cone shaped as is illustrated in FIG. 4.

Surrounding the tapered tip 410 is a tip section 420. Surrounding the tip section 420 is a coating 422. The coating in some embodiments may be a bio-compatible coating. The material of the tip section 420 may be identical with the coating 422 or it may be of another material. For instance it may contain one or more nitinol strands. The material of the tip section 420 can be chosen to give a desirable flexibleness to the distal tip region 404. FIG. 4 has shown the overall structure of a guidewire. In the following Figs. various types of sensors and cables are incorporated into the prototype guidewire design shown in FIG. 4. The actual configuration of the guidewires shown in the following Figs. may be adapted or changed in accordance with the example shown in FIG. 4. FIG. 4 and other figures illustrating guide wires are not drawn to scale.

Guidewires are required for most vascular interventions. Standard guidewires are made from metals and cannot be used in MR due to MR-related RF heating. MR-guidewires that do not contain long conductive structures but instead consist of a PEEK plastic core and a fiber compound core have been proposed before.

PEEK is hardly strong enough to realize guidewires with clinical performance especially at low diameters. A fiber compound consists of a multitude of thin fibers, which are embedded in and hold together by a plastic matrix material. The composite shaft comprising fibers may be a fiber compound. The process for production of the fiber compound is known as pultrusion and can be imagined as an extrusion process as performed for plastic tubing together with a fiber bundle. Pultrusion similarly to extrusion may be performed as an endless process. The components (i.e., dielectric-fibers, matrix material type) and the parameters (i.e., temperature, pultrusion speed, pressure at nozzle) are adapted to produce a stiff guidewire core. A fiber compound may for example consist of consisting of 12 μm thick fibers embedded in a plastic matrix material.

Guidewires typically have a tip section with continuously increasing floppiness. This prevents injury of the intima and allows navigation into vessel branches. For fiber-reinforced guidewires, this raises the problems of creating a smooth transition from a relatively stiff fiber-reinforced main section to the floppy tip section and the realization of the floppy section itself. A floppy tip section may be constructed, for example, by shafting (gluing) a tip section made from nitinol as conventionally used to the main section made from the fiber-reinforced material.

A feature of some embodiments of the invention is to provide an MR-guidewire with a core that is completely made from fiber-reinforced material up to the tip without the need for attachment of a separate tip section. Hence, the danger breaking off is abandoned. An even more important feature is that such a guidewire enables the integration and wiring of active components and sensors.

The introduction of active components or sensors into the tip and the change of mechanical parameters of the tip section cannot be achieved during the pultrusion process of the fiber-reinforced core because pultrusion only works as an endless process.

In some embodiments It is therefore proposed to first remove the matrix material, or matrix material material, in the tip section of a guidewire core again after the core has been pultruded and cut to length. Then, active components are introduced and wired, and at last, the tip is rebuilt to realize a floppy tip section.

The matrix can be removed by any appropriate process or a combination of processes, including resolution by a solvent, thermal treatment if the matrix is a thermoplast, oxidative removal of the organic material in a wet process, or other chemical processes.

Partial or complete removal can be applied. Partial removal may leave a central inner section of the core intact and only outer fibers are exposed and re-embedded in a softer matrix. This is efficient because the outer sections of the core contribute much more to the overall stiffness than the inner sections. An intact inner core may simplify the rebuilding process of the tip. Secondly, it may prevent breakage of the finished wire if there is a hard transition from original to new soft matrix material.

As a preparation step for removal or as an alternative to removal the matrix may be weakened or modified by chemical reactions, by ionizing or UV radiation, by mechanical treatment or other types of treatment. Weakening may be used to achieve the increased floppiness of the tip section directly.

If the fibers of the tip section are partially or completely exposed, objects can be incorporated into the tip section. In this stage, any type of sensors (pressure, temperature, flow, acceleration, can be introduced and wired to respective wires or optical fibers. Such wires or fibers preferably have been co-pultruded in the endless process. For intrinsic fiber-optic sensors wiring is not required, because the fiber itself represents the sensor. However, intrinsic sensors may have to be prepared for access to the quantity to be measured, which may be hard to realize in the initial pultrusion process. An obvious example is an intrinsic fiber-pressure sensor. It will not work being rigidly embedded in the fiber-compound surrounded by matrix and other fibers as after the pultrusion. Matrix removal enables to single out such a fiber-sensor from the fiber bundle and to position and prepare it within the tip section such that it has access to surrounding pressure, which may even require to apply a window in the coating. Another example is the preparation of an optical fiber that will be used to transmit/collect light from tissue for illumination/ablation or optical signal reception of some form. Such a fiber may be located to the outside of the bundle, embedded in the coating near the surface or below an optical window, equipped with a microprism or microlens.

Co-pultruded electrical wires may singled-out and connected to electrical sensors. Similarly to wiring of wires to sensors in the tip, matrix removal may be used at the proximal end of the device to connect wires or fibers to respective read-out hardware.

Finally, the same or a different, preferable softer matrix material (matrix material) is applied to rebuild the matrix around the exposed fibers and other components by compression molding or a similar process. The fibers may be trimmed before refixation similarly to the shape of the nitinol section or to another appropriate shape facilitating a tip with increasing floppiness. Additional components for mechanical reinforcement may be added, e.g. one or several thin nitinol wires.

The different matrix material in the tip section may not only be used to change the mechanical properties but also to realize a different dotation with substances that provide visibility in MRI or X-ray and CT.

Fiber-optic shape sensing may be included as one form of sensors Optical methods are used to measure the strain in a set of fibers which are rigidly attached to each other, from which the shape in 3D and also the temperature profile can be calculated. Two principles have been used to measure fiber-shape, fiber-bragg-gratings and characteristic Rayleigh scatter patterns.

Highly resistive wires may be included into core or between core and coating Such wires are known to prevent MR-induced RF heating from their use in catheters. They can be used for temperature sensing when fitted to a thermistor as well as for sensing of intracardiac electrophysiology signals.

Pressure sensor, e.g. fiber-optic with 0.2 mm outer diameter of actual sensor OPP-M by OPSENS, a MEMS-based fiber optic pressure sensor designed for human and animal physiological pressure measurements.

These miniature 0.25 mm OD and 0.40 mm OD sensors are intended for use in catheters, guide-wires or other devices enabling minimally invasive physiology pressure measurement. Its novel patent pending design eliminates moisture-induced drift and minimizes thermal zero shift.

Various companies have commercialized fiber-optic temperature sensors, also for integration into intravascular devices.

A acceleratometer may also be operated via fiber-optics and therefore used as a sensor in a guidewire.

For the matrix (matrix material) and coating materials Thermoplasts (Polyurethane, polypropylene, . . . ) as well as epoxies can be used. For a previous passive guidewire, Krueger et al used the matrix material epoxy in combination with fibers primarily optimized for 0.018-, 0.026-, and 0.032-inch shaping tools to allow for variable guidewire stiffnesses and sizes.

As coatings, polyurethanes (PU), polyether/amide blocl copolymers (PEBAX), polypropylene (PP) and other materials as for standard guidewires and catheters can be used.

Figure 5:
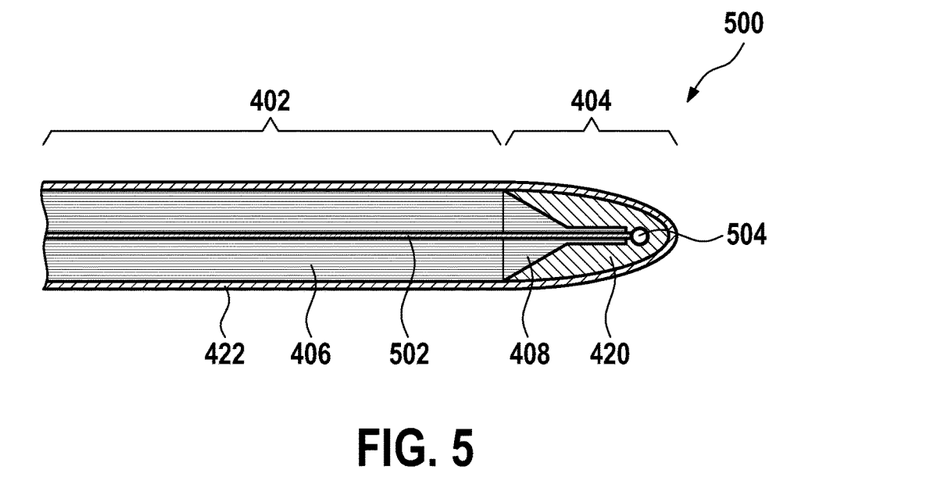
FIG. 5 illustrates a guide wire according to a further embodiment of the invention.

FIG. 5 shows a further embodiment of a guidewire 500 according to an embodiment of the invention. The embodiment shown in FIG. 5 is similar to the embodiment shown in FIG. 4. In this embodiment a cable 502 is shown as being integrated into the composite shaft 406, 408. For instance the cable 502 may be a fiber optic or a resistive wire. At the end of the cable 502 is a sensor 504 embedded into the tip section 420. Various types of sensors 504 may be integrated into the guidewire 500.

Figure 6:
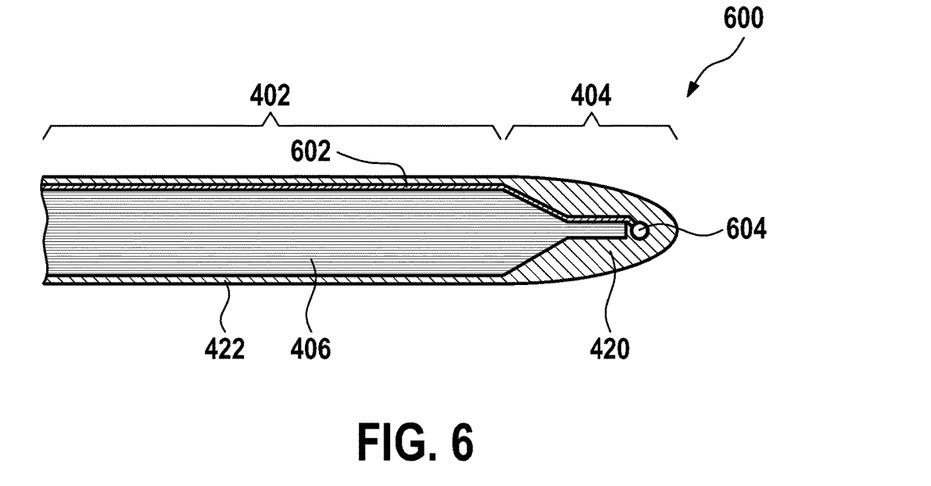
FIG. 6 illustrates a guide wire according to a further embodiment of the invention.

FIG. 6 shows a further embodiment of a guidewire 600 according to an embodiment of the invention. In this embodiment the composite shaft 406 only has a single matrix material type. Also in this embodiment a cable 602 is attached to an exterior surface of the composite shaft 406. The cable 602 runs the length of the composite shaft 602 to the tip section 420 where it is connected to a sensor 604. In this embodiment the tip section 420 and the coating 422 are made of the same material. In another variation of this embodiment the tip section 420 and the coating 422 are made of different materials as is illustrated in FIG. 5.

Figure 7:
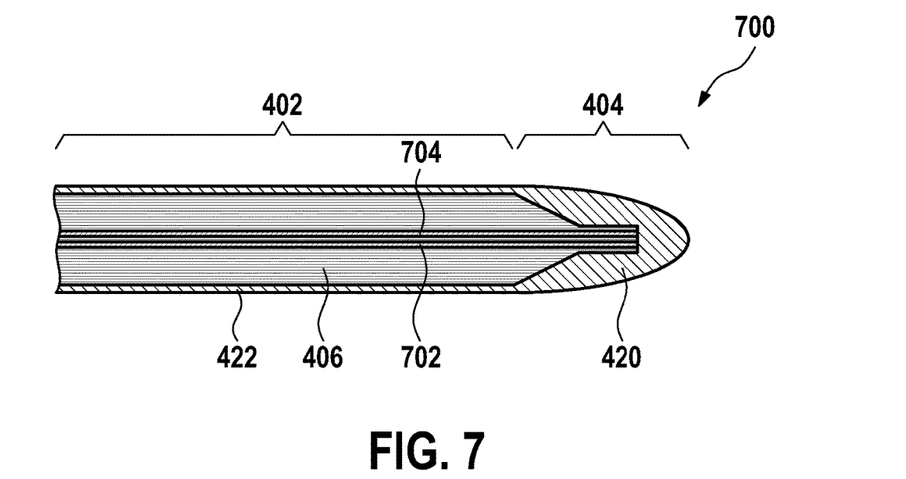
FIG. 7 illustrates a guide wire according to a further embodiment of the invention.

FIG. 7 shows a guidewire 700 according to a further embodiment of the invention. The embodiment in FIG. 7 is similar to that shown in FIG. 4. In this embodiment there is only a single composite material 406 making up the composite shaft. Within the composite shaft 406 there is a first fiber optic 702 and a second fiber optic 704. The at least two fiber cores are spaced apart from each other to prevent load coupling between the fiber cores. A frequency domain reflectometer may then transmit light to and from the optical fibers. This may be then used for determining the position and/or shape sensing using Rayleigh scattering. A similar arrangement may also be used for constructing an optical fiber Bragg grating strain-sensor to detect deflection of the guidewire 700. In this embodiment the tip section 420 and the coating 422 are made of the same material. In another variation of this embodiment the tip section 420 and the coating 422 are made of different materials as is illustrated in FIG. 5.

Figure 8:
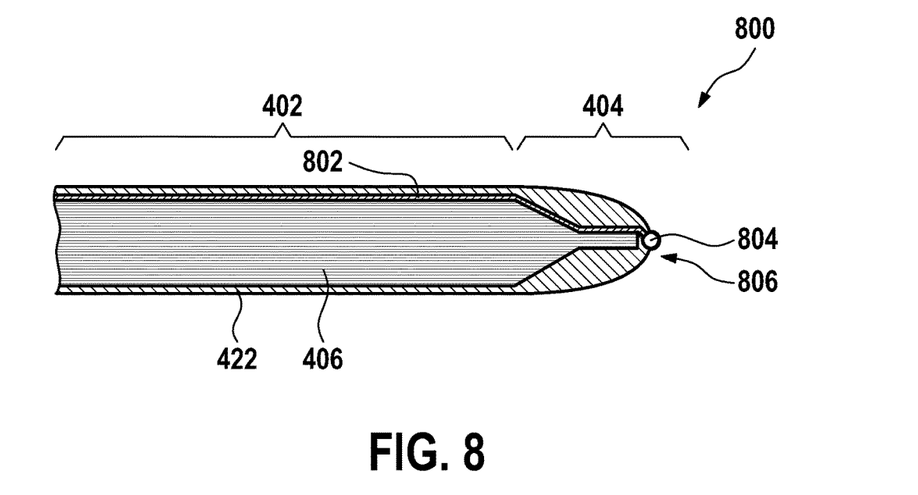
FIG. 8 illustrates a guide wire according to a further embodiment of the invention.

FIG. 8 shows further embodiment of a guidewire 800 according to an embodiment of the invention. In this embodiment there is a resistive wire 802 attached to an outer surface of the composite shaft 406. On a surface of the tip 806 there is an electrode 804. The resistive wire 802 is connected to the electrode 804. The guidewire 800 may then be used as an electrophysiological potential sensor for example for an ECG machine. In this embodiment the tip section 420 and the coating 422 are made of the same material. In another variation of this embodiment the tip section 420 and the coating 422 are made of different materials as is illustrated in FIG. 5.

Figure 9:
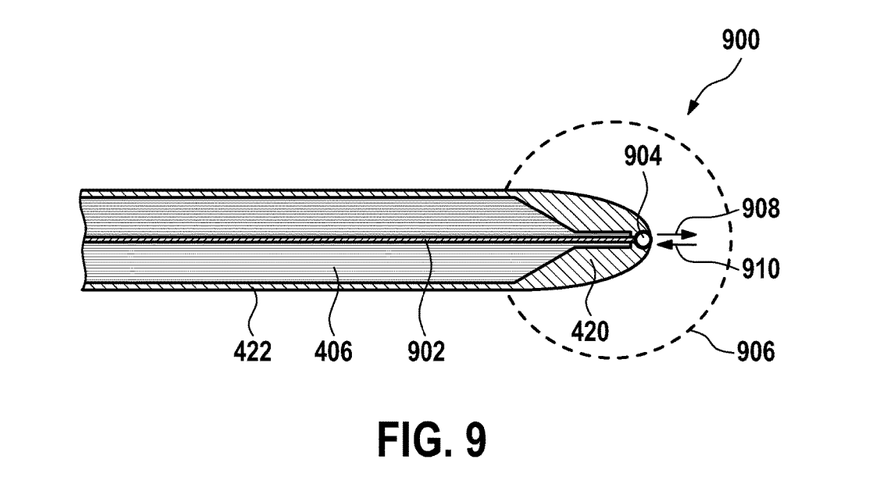
FIG. 9 illustrates a guide wire according to a further embodiment of the invention.

FIG. 9 shows a further embodiment of a guidewire 900 according to an embodiment of the invention. In this example there is a single fiber optic 902 embedded within the composite shaft 406. At the tip region 420 there is an optical coupling 904 connected to the fiber optic 902. The optical coupling 904 allows light 908 to be emitted into a region 906 surrounding the tip 420. The optical coupling 904 also allows light 910 to be focused back into the fiber optic 902 to be analyzed. Such a guidewire 900 could for instance be used for an optical reflection spectrum sensor, an optical transmission spectrum sensor, or an optical fluorescence spectrum sensor. In this embodiment the tip section 420 and the coating 422 are made of the same material. In another variation of this embodiment the tip section 420 and the coating 422 are made of different materials as is illustrated in FIG. 5.

Figure 10:
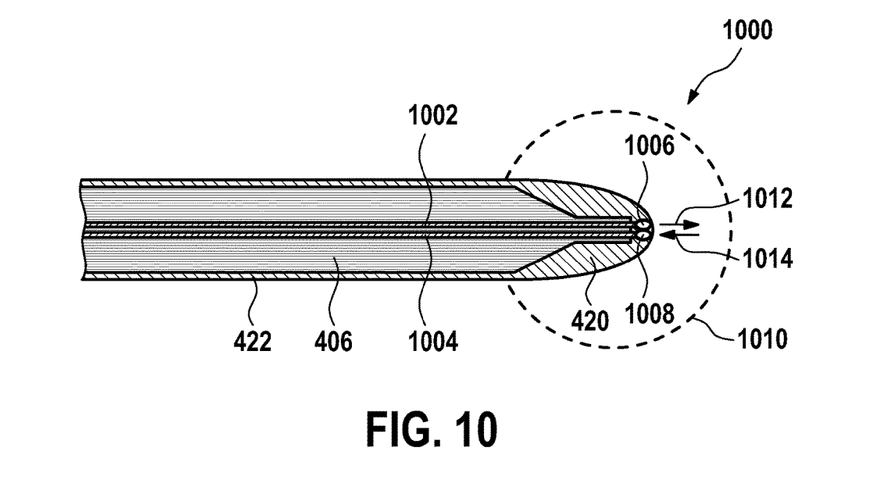
FIG. 10 illustrates a guide wire according to a further embodiment of the invention.

FIG. 10 shows a further embodiment of a guidewire 1000 according to the invention. The embodiment shown in FIG. 10 is similar to that in FIG. 9 except in this case there is a first fiber optic 1002 and a second fiber optic 1004. The first fiber optic 1002 is coupled to a first optical unit 1006 and the second fiber optic 1004 is connected to a second optical unit 1008. Optical unit 1006 focuses light that travels through the first fiber optic 1002 towards the tip region 420. Light is then emitted from the first optical unit 1006 into a region 1010 surrounding the tip 420. Light is then absorbed 1014 by optical unit 1008 which then focuses the light 1014 into fiber optic 1004 where it may be analyzed. Such a guidewire 1000 may be useful as an optical reflect spectrum sensor, an optical transmission spectrum sensor, and for an optical fluorescence spectrum sensor. In this embodiment the tip section 420 and the coating 422 are made of the same material. In another variation of this embodiment the tip section 420 and the coating 422 are made of different materials as is illustrated in FIG. 5.

Figure 11:
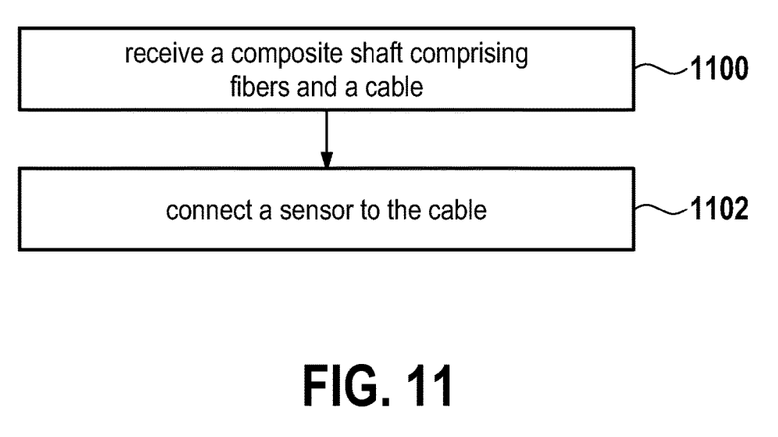
FIG. 11 shows a flowchart which illustrates a method according to a further embodiment of the invention.

FIG. 11 shows a flowchart which illustrates a method according to a further embodiment of the invention. First, in step 1100 a composite shaft which is formed from fibers and a cable is received. Next in step 1102 a sensor is connected to the cable.

Figure 12:
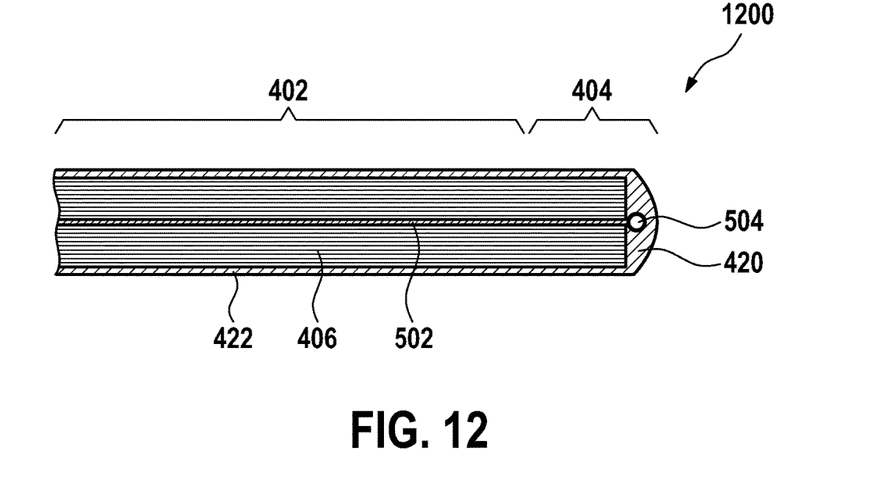
FIG. 12 illustrates a guide wire according to a further embodiment of the invention

FIG. 12 show a guidewire 1200 according to a further embodiment of the invention. The guidewire 1200 is similar to the embodiment shown in FIG. 5 except that the guidewire 1200 lacks a tapered region in its distal tip region. In this embodiment the tip section 420 and the coating 422 are made of the same material. In another variation of this embodiment the tip section 420 and the coating 422 are made of different materials as is illustrated in FIG. 5. The composite shaft in both the shaft region 402 and the distal tip region 404 are made of a composite with the same matrix material 406.

Figure 13:
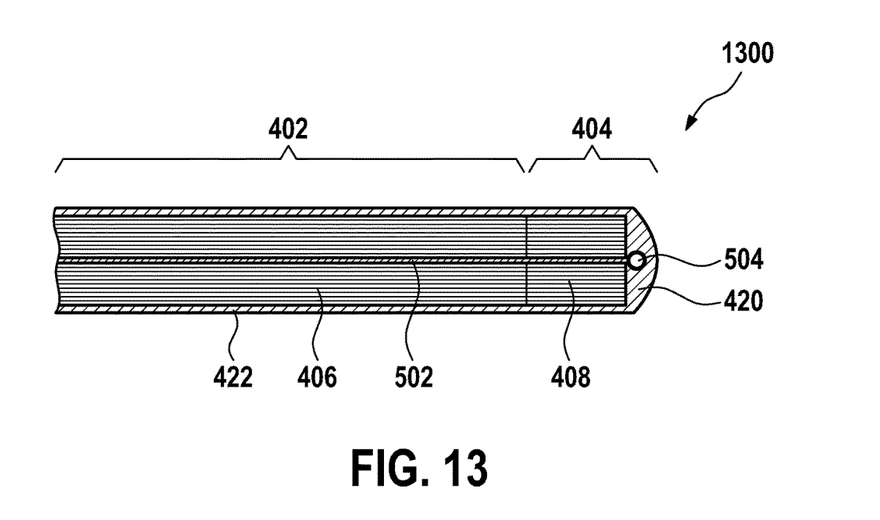
FIG. 13 illustrates a guide wire according to a further embodiment of the invention.

FIG. 13 shows a guidewire 1200 according to a further embodiment of the invention. The guidewire 1300 is similar to the embodiment shown in FIG. 12 in that it also lacks a taper in its distal tip region 404. In this embodiment the tip section 420 and the coating 422 are made of the same material. In another variation of this embodiment the tip section 420 and the coating 422 are made of different materials as is illustrated in FIG. 5. The composite shaft in the shaft region 402 has a first matrix material 406 and composite shaft in the distal tip region 404 has a second matrix material 408. The use of a second matrix material may allow the flexibility of the distal tip region to be controlled without the use of a taper. For instance the second matrix material may have a flexibility greater than that of the first matrix material.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 400 guide wire
402 shaft region
403 length extension
404 distal tip region
406 composite with first matrix material
408 composite with second matrix material
410 taper
412 length
414 length of taper
416 outer diameter
418 inner diameter
420 tip section
422 coating
500 guide wire
502 cable
504 sensor
600 guide wire
602 cable
604 sensor
700 guide wire
702 fiber optic
704 fiber optic
800 guide wire
802 resistive wire
804 electrode
806 surface of tip
900 guide wire
902 fiber optic
904 optics
906 region surrounding tip
908 emitted light
910 received light
1000 guide wire
1002 fiber optic
1004 fiber optic
1006 optics
1008 optics
1010 region surrounding tip
1012 emitted light
1014 received light
1200 guide wire
1300 guide wire

The invention claimed is:
1. A guide wire comprising:
a composite shaft comprising: a shaft region comprising a first matrix material having a first flexibility; and a distal tip region comprising a second matrix material having a second flexibility, wherein the composite shaft is tapered in the distal tip region;

one or more cables aligned with a length of the shaft region, wherein the cables extend at least partially into the distal tip region; and a sensor provided in the distal tip region and connected to the one or more cables.

2. The guide wire of claim 1, wherein the cable is included within the composite shaft.

3. The guide wire of claim 2, wherein the cable is a fiber optic cable.

4. The guide wire of claim 3, wherein the sensor is selected from at least one of a thermometer, an accelerometer, a pressure sensor, an optical reflection spectrum sensor, an optical transmission spectrum sensor, and/or an optical fluorescence spectrum sensor.

5. The guide wire of claim 3, wherein the fiber optic cable is, selected from at least two or more single core optical fibers, a sensor, and a fiber optic position and/or shape sensor.

6. The guide wire of claim 1, wherein the cable is attached to the composite shaft.

7. The guide wire of claim 1, wherein the cable is a wire.

8. The guide wire of claim 7, wherein the sensor is selected from at least one of a temperature sensor, a pressure sensor, and an electrophysiological potential sensor.

9. The guide wire of claim 1, wherein the second flexibility is higher than the first flexibility.

10. The guide wire of claim 1, wherein the taper within the distal tip region is wider at the shaft region than in the distal tip region.

11. A catheter system comprising:
a catheter; and
a guide wire according to claim 1, wherein the guide wire is configured for guiding the catheter.

12. A method of manufacturing a guide wire, the method comprising:
forming a composite shaft comprising a shaft region of a first matrix material of a first flexibility and a distal tip region of a second matrix material having a second flexibility;
tapering the composite shaft in the distal tip region;
aligning one or more cables with a length of the shaft region;
extending the cables at least partially into the distal tip region;
providing an anatomical property sensor for determining properties of tissue in the distal tip region; and
connecting the sensor to the cables.

13. The method of claim 12, wherein the method further comprises—incorporating the cable into the composite shell using a pultrusion process.

14. The method of claim 12, further comprising removing the matrix material at the distal tip region.

15. The method of claim 12, further comprising shaping the taper in the distal tip region wide at the shaft region and narrowing in the distal tip region.

16. The guide wire of claim 1, wherein the sensor is configured to determine properties of tissue surrounding the distal tip region.

17. The guide wire of claim 1, wherein the shaft including an extended flexible resin with fibers extending along a length of the shaft at least partially into the distal tip region for steering the distal tip region of the shaft through the anatomical region.

18. The guide wire of claim 17, wherein the cable includes an optic fiber coextruded with the flexible resin and the fibers.

19. A guide wire for guiding a catheter through an anatomical region of a patient in a magnetic resonance environment, the guide wire comprising:
a composite shaft including a shaft region and a closed, tapered distal tip region, the distal tip region being more flexible than the shaft region, the shaft including a flexible resin with fibers extending along a length of the shaft at least partially into the distal tip region for steering the distal tip region of the shaft through the anatomical region;
a sensor embedded in the distal tip region and configured to determine properties of tissue surrounding the distal tip region; and
a cable connected to the sensor and extending through the shaft, the cable being configured to communicate the determined tissue properties.

20. The guide wire of claim 19, wherein the cable includes an optic fiber coextruded with the flexible resin and the fibers.

* * * * *